(12) United States Patent
Almeida Ferreira et al.

(10) Patent No.: US 9,809,550 B2
(45) Date of Patent: Nov. 7, 2017

(54) QUINOLYL HYDRAZONES FOR THE TREATMENT OF TUBERCULOSIS AND RELATED DISEASES

(71) Applicant: TECNIMEDE SOCIEDADE TECNICO-MEDICINAL S.A., Sintra (PT)

(72) Inventors: Ana Lucia Almeida Ferreira, São Gregório CLD (PT); Ana Sofia Lopes, Loures (PT); Augusto Eugenio Pardal Filipe, Lisbon (PT); Pedro Filipe Eufrasio Pedroso, Lisbon (PT); Susana Marques De Almeida Pecorelli, Alcabideche (PT); Carlos Caixado, Mafra (PT)

(73) Assignee: TECNIMEDE SOCIEDADE TECNICO-MEDICINAL S.A., Sintra (PT)

( * ) Notice: Subject to any disclaimer, the term of this patent is extended or adjusted under 35 U.S.C. 154(b) by 26 days.

(21) Appl. No.: 14/443,787

(22) PCT Filed: Nov. 20, 2013

(86) PCT No.: PCT/PT2013/000069
§ 371 (c)(1),
(2) Date: May 19, 2015

(87) PCT Pub. No.: WO2014/081325
PCT Pub. Date: May 30, 2014

(65) Prior Publication Data
US 2015/0299128 A1 Oct. 22, 2015

(30) Foreign Application Priority Data

Nov. 20, 2012 (PT) .................................... 106651

(51) Int. Cl.
C07D 215/38 (2006.01)
A61K 31/47 (2006.01)
A61K 31/4709 (2006.01)
(52) U.S. Cl.
CPC ............ *C07D 215/38* (2013.01); *A61K 31/47* (2013.01); *A61K 31/4709* (2013.01)
(58) Field of Classification Search
CPC ... C07D 215/38; A61K 31/47; A61K 31/4709
See application file for complete search history.

(56) References Cited

U.S. PATENT DOCUMENTS

2008/0118576 A1* 5/2008 Theodorescu ....... A61K 31/337
424/649
2012/0282629 A1* 11/2012 Wanker ................. C07C 251/86
435/7.9

FOREIGN PATENT DOCUMENTS

WO 2011/047814 A1 4/2011

OTHER PUBLICATIONS

Lukov et al., 31(10) Russian J. Coord. Chem. 732-736 (2005) (CAS Abstract).*
International Search Report dated Jun. 2, 2014 from the International Bureau in counterpart International Application No. PCT/PT2013/000069.
Amit Nayyar et al: "Synthesis and anti-tuberculosis activity of 2,4-disubstituted quinolines", Indian Journal of Chemistry, vol. 47B, Jan. 1, 2008 (Jan. 1, 2008), pp. 117-128, XP055098766, Table I, particularly compounds lOd,lOg,lOh, lid, Hi,llj, 12d, 12h, 12i, 14d, 14j; p. 122, left col. 1. 10-15.
Douglas G. Berge: "Synthesis of new 2-pyridylhydrazones and 2-quinolylhydrazones containing 2-thiophene or 2-furan groups", Journal of Chemical & Engineering Data, vol. 28, No. 4, Oct. 1, 1983 (Oct. 1, 1983), pp. 431-432, XP055099248, ISSN: 0021-9568, DOI: 10.1021/je00034a025 Table I, compounds X, XII, XIII.
Marcelle De L. Ferreira et al: "Synthesis and Antitubercular Activity of Heteroaromatic Isonicotinoyl and 7-Chloro-4-Quinolinyl Hydrazone Derivatives", The Scientific World Journal, vol. 10, Jan. 1, 2010 (Jan. 1, 2010), pp. 1347-1355, XP055099059, DOI: 10.1lO0/tsw.2O10.124 the whole document.
Lukov et al., "Crystal Structure and Physicochemical Properties of New Copper(II) Complexes with 2-Hydrazinoquinoline Salicylidenehydrazones", Russian Journal of Coordination Chemistry, vol. 31, No. 10, 2005, pp. 732-736. Translated from Koordinatsionnaya Khimiya, vol. 31, No. 10, 2005, pp. 770-774. Original Russian Text Copyright © 2005 by Lukov, Akeksandrov, Dontsova, Kogan, Popov.

* cited by examiner

Primary Examiner — Timothy R Rozof
(74) Attorney, Agent, or Firm — Sughrue Mion, PLLC

(57) ABSTRACT

The invention provides quinolyl-hydrazones of Formula I, or pharmaceutically acceptable salts, esters, solvates, isomers and prodrugs thereof as well as pharmaceutical compositions containing these compounds for use in the prophylactic and/or therapeutic treatment of tuberculosis and related diseases, such as, diseases caused by nontuberculous mycobacteria and/or caused by *Micobacterium leprae*.

13 Claims, 2 Drawing Sheets

QUINOLYL HYDRAZONES FOR THE TREATMENT OF TUBERCULOSIS AND RELATED DISEASES

FIELD OF THE INVENTION

The invention relates to compounds and pharmaceutical compositions which are useful as pharmaceutical agents for treating tuberculosis and related diseases.

BACKGROUND OF THE INVENTION

There are more than 120 members of the genus *Mycobacterium*, which are diverse in pathogenicity, in vivo adaptation, virulence, response to drugs and growth characteristics. Mycobacterial diseases are caused by organisms of the *Mycobacterium tuberculosis* Complex (MtbC) like *Mycobacterium tuberculosis* (Mtb), *Mycobacterium bovis*, *Mycobacterium africanum*, *Mycobacterium canetii* and *Mycobacterium microti*. Mycobacteria other than MtbC and *Mycobacterium leprae* are known as non-tuberculous mycobacteria (NTM) and can cause also human and animal diseases as is the case for *Mycobacterium avium* complex (MAC), *Mycobacterium smegmatis, Mycobacterium gordonae, Mycobacterium kansasii, Mycobacterium terrae, Mycobacterium scrofulaceum, Mycobacterium vaccae, Mycobacterium marinum, Mycobacterium lentiflavum, Mycobacterium fortuitum, Mycobacterium chelonae* and *Mycobacterium abscessus*.

Most human tuberculosis (TB) is caused by Mtb but some cases are due to *Mycobacterium bovis*, which is the principal cause of tuberculosis in cattle and many other mammals, or *Mycobacterium africanum*.

The consequences of tuberculosis on all human societies are dramatic: worldwide, one person out of three is infected with Mtb.

The lung is the main entrance gate of Mtb in the body and, consequently, TB is primarily a disease of the lungs. *Mycobacterium tuberculosis* causes a focal infection in the site where it is deposited after inhalation. If the infection cannot be contained at the local level, bacilli dissemination is produced initially by hematogenic route, probably inside phagocytic cells, towards different organs and, eventually, to the contiguous pleura. It reaches hilar lymph nodes via the lymphatic route, and from there, a second systemic dissemination can occur, through the thoracic duct and superior vena cava, with the development of local foci in the lungs. Extrapulmonary foci can also be produced by hematogenic and lymphatic dissemination. Tuberculosis can proceed to a generalized infection ("miliary tuberculosis").

The clinical manifestations of TB depend on the local organic defenses on the sites of bacilli multiplication. Primary TB infection occurs commonly during childhood and most of the times, causes no apparent symptoms and stays latent for life or until reactivation. Occasionally cause malaise, low-grade fever, erythema nodosum and phlyctenular conjunctivitis. In seriously immunodepressed patients it can develop into a disseminated form, which is sometimes fatal. Miliary tuberculosis results from the massive hematogenic dissemination of Mtb during the primary infection.

The development of clinical TB will occur in 5%-10% of infected persons at some point in their lives. The existence of post-primary TB, also known as secondary TB, means that the infection can progress after the development of an adequate specific immune response. This TB episode can develop in two ways: by inhalation of new bacilli or by reactivation of the primary focus.

There are factors involved in increased risk of developing TB, of which the most important are those interfering directly with host immunity. Diseases and conditions that weaken immunity, such as malnutrition, alcoholism, illicit drug abuse, advanced age, human immunodeficiency virus (HIV) infection or acquired immunodeficiency syndrome (AIDS), diabetes mellitus, gastrectomy, chronic renal insufficiency, chronic liver disease, silicosis, paracoccidioidomycosis, leukemias, solid tumors, prolonged treatment with corticosteroids, immunosuppressive drug treatments, organ transplant, systemic lupus erythematosus, treatment with anti-tumor necrosis factor (TNF) antibodies and hereditary features, are factors that facilitate the development of TB disease. In industrialized countries the increased survival rates have resulted in larger elderly populations with an increased risk of reactivation of the infection. Tuberculosis in the elderly may be due also to a newly acquired infection. Congenital T.B. is considered a rare event in the whole spectrum of TB presentations. This infection is caused by lymphohematogenous spread during pregnancy from an infected placenta or aspiration of contaminated amniotic fluid.

Additional factors include the infective bacterial load, virulence of Mtb and host genetic susceptibility.

Pulmonary TB is the most common form of post-primary disease. The natural evolution of post-primary lesions in immunocompetent persons can lead to dissemination and death in about 50% of cases, and to chronicity in about 25% to 30%.

After penetration into the organism through the respiratory route, Mtb can multiply in any organ during the primary infection, before development of the specific immune response. After this, tubercle bacilli can multiply at any time when there is a decrease in the host's immune capacity to contain the bacilli in their implantation sites. The extrapulmonary tuberculosis can affect any other organ of the body, including lymph nodes, pleura, genitourinary system, central nervous system, osteoarticular system, gastrointestinal system, skin and soft tissues and eye.

Tuberculosis accounts for 2.5% of the global burden of disease and holds the seventh place in the global ranking of causes of death. In 2010, there were 8.8 million incident cases of TB, 1.1 million deaths from TB among HIV negative people and an additional 0.35 million deaths from HIV-associated TB. Without treatment, a person with active TB will infect an average of 10 to 15 other people per year.

The minimum period of treatment for active, drug-sensitive TB is 6 months, and will typically use a starting regimen of four drugs denominated first-line drugs: isoniazid (INH), rifampicin (RMP), pyrazidamine (PZA) and ethambutol (EMB). However, when administered in real-world settings, the regimen's flaws become apparent. Treatment of drug-resistant TB is even lengthier, taking 18-24 months or longer.

The selection of the drug regimen must be done considering at least the following factors: disease localization and severity, result of sputum smear microscopy, HIV co-infection, prevalence of drug resistance in the setting, availability of drugs, cost of treatment and medical supervision, whether the patient has previously received any anti-tuberculosis drug, the country's budget, health coverage by public health services and qualifications of health staff.

Human immunodeficiency virus infection has clearly had a profound effect on TB epidemiology. Human immunodeficiency virus infection is a potent risk factor for TB and both form a lethal combination, each speeding the other's progress. Not only does HIV increase the risk of reactivating latent Mtb and the risk of rapid TB progression soon after Mtb infection or reinfection. Those who have latent tuberculosis have a 10% lifetime risk of progressing to active infection, with half (5%) occurring within 1-2 years after initial infection. In persons co-infected with Mtb and HIV, however, the annual risk can exceed 10%.

The resistance mechanisms can be divided in natural and acquired. The natural drug resistance of Mtb is an important obstacle for the treatment and control of TB. This resistance has traditionally been attributed to the unusual multi-layer cell envelope and/or active multidrug efflux pumps.

The acquired drug resistance is mediated by mutations in chromosomal genes. So far, no single pleiotropic mutation has been found in Mtb to cause a multi-drug resistant (MDR) phenotype. The MDR phenotype is caused by sequential accumulation of mutations in different genes involved in resistance to individual drugs, due to inappropriate treatment or poor adherence to treatment. However, it is important to observe that some resistant strains do not present these classic mutations, suggesting the possibility of the existence of other mechanisms such as efflux pumps and alterations in the permeability of the cell wall.

Multidrug-resistant TB (MDR-TB) is defined by resistance to the two most commonly used drugs in the current four-drug (or first-line) regimen, INH and RMP. According to the World Health Organization (WHO), Eastern Europe's rates of MDR-TB are the highest, where MDR-TB makes up 20 percent of all new TB cases. During the late 1980s and early 1990s, outbreaks of MDR-TB in North America and Europe killed more than 80% of those who contracted the disease. Today, MDR-TB is also quite common in India and China, as the two countries combined account for more than half of the global MDR-TB burden.

Drug-resistant TB is the man-made result of interrupted, erratic, or inadequate TB therapy, and its spread is undermining efforts to control the global TB epidemic. Multiple drug resistant and extensively drug resistant tuberculosis (XDR-TB) develop when the long, complex, decades-old TB drug regimen is improperly administered, or when people with TB stop taking their medicines before the disease has been fully eradicated from their body. Once a drug-resistant strain has developed, it can be transmitted directly to others just like drug-susceptible TB.

Treatment for MDR-TB consists of what are called second-line drugs. These drugs are administered when first-line drugs fail. Treatment for MDR-TB is commonly administered for 2 years or longer and involves daily injections. Many second-line drugs are toxic and have severe side effects. Further, the cost of curing MDR-TB can be staggering—literally thousands of times as expensive as that of regular treatment in some regions—posing a significant challenge to governments, health systems, and other payers.

More recently emerged extensively drug-resistant Mtb strains that are the agents of extensively drug-resistant tuberculosis (XDR-TB). This form of the disease is defined as TB that has developed resistance to at least RMP and INH, as well as to any member of the quinolone family and at least one of the following second-line anti-TB injectable drugs: kanamycin (KAN), capreomycin (CAP) or amikacin (AMIC).

In recent decades the development of MDR-TB and XDR-TB, and the presence of HIV have combined to increase the global threat to public health posed by TB. In addition to increasing individual susceptibility to TB following Mtb infection, a high burden of HIV-associated TB cases also expands Mtb transmission rates at the community level, threatening the health and survival of HIV-negative individuals as well. In several countries, HIV has been associated with epidemic outbreaks of TB. Many of the reported outbreaks involved MDR strains, which respond poorly to standard therapy—the growing burden of TB.

The long and complex regimen is burdensome for patients, even when taken under direct observation by a healthcare worker or community member, as recommended by WHO. As a result, many patients do not or cannot complete their treatment, which leads to the development of drug-resistant strains. While MDR-TB is a man-made issue, research has shown that those strains are now being transmitted from patient to patient. Second-line drugs are also much more toxic and considerably more expensive than the standard first-line anti-TB regimen.

Furthermore, current first-line treatment regimens are not compatible with certain common antiretroviral (ARV) therapies used to treat HIV/AIDS. To avoid drug-drug interactions in co-infected patients, the treatment regimen for one of the diseases must be suboptimally modified. Therefore, new drugs are needed that will be effective in treating children, and latent TB infection (an asymptomatic infection) and will be compatible with antiretroviral therapy. Additionally, new regimens need to be affordable and easily managed in the field.

The introduction of new drugs, preferably with novel mechanisms of action, which will be active against current drug-resistant and extensively drug-resistant strains, and fewer TB drug side effects, will hopefully allow for a shorter TB regimen for both drug-sensitive and drug-resistant disease (MDR-TB and XDR-TB). Shortening treatment to four or two months or even less should increase cure rates, improve patient adherence, and lessen the likelihood of developing drug resistance. This poses a massive challenge to controlling these twin epidemics, given that an estimated one-third of the 40 million people living with HIV/AIDS worldwide are co-infected with TB. The deadly synergy of these two diseases demands first-line treatments that can be fully harmonized.

Drug-resistant TB is difficult, complicated, and expensive to treat. Treatment relies on second-line drugs, and is commonly administered for 2 years or longer. It includes daily injections, and often causes severe side effects. Of those who do, nearly half will still die. What's worse, some resistant strains are virtually untreatable with any existing antibiotics. The complexity and prohibitive cost of MDR-TB treatment means that fewer than 3% of the world's MDR-TB patients receive proper treatment. Without a significantly simpler, faster cheaper, oral treatment for MDR-TB, countries cannot scale up treatment to serve their populations. Without new, simple, and affordable treatments for MDR-TB, this is not realistically possible.

Extensively drug-resistant TB (XDR-TB) is emerging as an even more ominous threat. This makes XDR-TB treatment extremely complicated, if not impossible, in resource-limited settings. It is estimated that 70% of XDR-TB patients die within a month of diagnosis. The most recent drug-resistance surveillance data issued by the WHO estimates that an average of roughly 5 percent of MDR-TB cases are XDR-TB.

When drug resistance develops, patients should be treated with a new combination containing at least three drugs that they had never received before (or that do not show cross-resistance with those to which resistance is suspected). In these conditions, the treatment is longer, more toxic, more expensive and less effective than regimens containing first-line drugs, and should be directly observed.

Since HIV/AIDS patients have a higher probability of acquiring TB (either pulmonary or extrapulmonary) or other mycobacterial opportunistic infections, particular drug regimens have been designed for treating active TB disease in them.

Also, the severity of adverse effects of anti-mycobacterial drugs (due to the interactions with anti-retroviral drugs) and mortality is higher among HIV-positive patients. Although, in general, HIV-positive patients respond well to a standard short-course treatment of TB, treatment failure due to malabsorption of antimycobacterial drugs has been reported. For example, rifamycins (rifampicin, rifabutin, etc.) have clinically relevant interactions with some drugs used in the antiretroviral therapy, since they induce the metabolism of anti-retroviral agents such as zidovudine, non-nucleoside reverse transcriptase inhibitors, and HIV protease inhibitors, whose concentrations may fall to sub-therapeutic levels. Then, rifamycin-free regimens have been suggested. They consist of INH, EMB, PZA, and streptomycin (SM), daily for two months, followed by INH, PZA, and SM two or three times weekly for seven months. However, it has also been described that the use of RIF throughout antituberculosis treatment improves outcome in HIV patients.

Chemoprophylaxis of TB is indicated for asymptomatic patients having a positive tuberculin skin test (TST) but not showing active disease (latent TB infection), especially when they are at risk of the disease (for example, HIV positive patients). Prophylaxis is most frequently achieved by the administration of INH only, at doses of 300 mg daily for six to nine months (although there is a risk of developing INH resistance). When resistance to INH is suspected, other regimens including RIF, PZA or EMB can be administered, although there is a greater chance of having adverse effects. In TB prophylaxis, RIF can be given concurrently with INH, reducing the prophylaxis treatment to three months.

Most drugs used in antituberculosis treatment (isoniazid, rifampicin, rifapentine, rifabutin, pyrazinamide, ethambutol and ethionamide) are commercially available as tablets or capsules and can therefore be taken orally. Isoniazid is also available as an elixir, in granules for pediatric use, and in aqueous solution for intravenous or intramuscular injection. Rifampicin is available in powder for preparing suspensions for oral administration, and also in aqueous solution for intravenous or intramuscular injection. The exceptions are the aminoglycosides (streptomycin, kanamycin, and amikacin) and capreomycin, which are only available as aqueous solutions for intravenous or intramuscular injection. Para aminosalicylic acid (PAS) is usually available as granules for mixing with food; tablets and solutions for intravenous administration can also be found. The fluoroquinolones are available as tablets or as aqueous solutions for intravenous injections.

Isoniazid, rifampicin and pyrazinamide can also be found in fixed-dose combination preparations. When available, the use of combination preparations is recommended. Indeed, by reducing the number of tablets to be taken, they facilitate the patient's adherence to treatment and supervision of therapy. Most importantly, this form of preparation minimizes the possibility of monotherapy and therefore, reduces the risk of drug resistance development.

The framework of mycobacterial infections and diseases all over the world requires the systematic search for new antimycobacterial drugs. Almost no new anti-tuberculosis drug classes have been developed over the last 40 years. In fact, once the industrialized countries felt confident in accomplishing TB control, the leading pharmaceutical industries lost interest in the development of antimycobacterial drugs.

The emergence of the HIV pandemic soon followed by the increase of MDR-TB and XDR-TB incidence rate, the prevalence of chronic diseases, the generalized use of immunosuppressive treatments, the increase in organ transplantation and the general increase of the prevalence of severe and moderately severe forms of immunodeficiency conditions in the population require an urgent investment in research and development to discover new candidate compounds to treat the drug-resistant TB, overcome the complex drug-drug interactions between antimycobacterial and antiviral or cytotoxic drugs.

Additionally, these efforts should be focusing in the development of a shorter and simpler regime for TB could improve treatment compliance, stop the spread and enable the global scale-up of MDR-TB and XDR-TB treatment. A shorter and simpler treatment will not only help cure those currently under care, but will also allow health workers to reach more people by reducing the burden on national TB programs.

The research and development of new medicines is an integral part of a comprehensive TB control plan. Without new and improved TB treatment regimens, including treatment for those suffering from MDR-TB and co-infected with HIV/AIDS, the reduction and eventual eradication of the disease cannot be achieved.

The nontuberculous mycobacteria (NTM) are for the most part ubiquitous environmental organisms found in soil and water that only rarely cause disease in humans. There are numerous species of NTM. Although regional variation in species isolation has been shown, the NTM most frequently isolated are those of the *Mycobacterium avium* Complex (MaC) *Mycobacterium intracellulare* and *Mycobacterium avium, Mycobacterium smegmatis, Mycobacterium kansasii, Mycobacterium fortuitum, Mycobacterium abscessus* and *Mycobacterium chelonae*.

These organisms have significant structural and biochemical similarities with Mtb. Because they are of significantly lower pathogenicity than Mtb, they are considered opportunistic pathogens. NTM are an important cause of morbidity and mortality, often in the form of progressive lung disease. Several species are associated with diseases of other organs or systems (ex.: skin and soft tissue, lymphatic and gastrointestinal systems). Disseminated disease due to NTM is primarily associated with AIDS and other forms of severe immunosuppression.

Human immunodeficiency virus infection also increases the risk of disease mediated by NTM. Patients with AIDS require new treatment modalities to approach MaC disease and prevention, such as combination therapy with nucleoside reverse transcriptase inhibitors and HIV protease inhibitors, as well as antimycobacterial prophylaxis. Most of the NTM except *Mycobacterium kansasii* are inherently resistant or partially susceptible to the standard anti-tubercular drugs.

Drug therapy for MAC disease involves multiple drugs; therefore, the risk of adverse drug reactions and/or toxicities is relatively high. In addition, the optimal therapeutic regimen has yet to be established. The recommended initial regimen for most patients with fibrocavitary or nodular/bronchiectatic MaC lung disease is a three times weekly regimen including clarithromycin or azithromycin, ethambutol and rifampin administered three times per week. Patients respond best to MaC treatment regimens the first time they are administered; therefore, it is very important that patients receive recommended multidrug therapy the first time they are treated.

The management of macrolide-resistant MaC involves complex clinical decision making, drug choices, and protracted duration of therapy, analogous to the drug management of MDR-TB.

Multiple factors can interfere with the successful treatment of MaC lung disease, including medication nonadherence, adverse events, prior therapy of MaC lung disease, lack of response to a medication regimen, or the emergence of a macrolide-resistant MaC strains.

The *Mycobacterium leprae* (Mlp) is the etiologic agent of leprosy, a chronic mycobacterial disease characterized by the involvement primarily of skin as well as peripheral nerves and the mucosa of the upper airway. The organism has never been grown in bacteriologic media or cell culture, but has been grown in mouse foot pads. The risk groups are the close contacts with patients with untreated, active, predominantly multibacillary disease and persons living in countries with highly endemic disease.

In 2002, Brazil, Madagascar, Mozambique, Tanzania, and Nepal had having 90% of cases. Worldwide, 1-2 million persons are permanently disabled as a result of leprosy. However, persons receiving antibiotic treatment or having completed treatment are considered free of active infection.

Multidrug therapy has not been implemented in many endemic areas. Nerve damage must be recognized and managed. Relapse rate after completion of short course multidrug therapy may rise.

Paucibacillary leprosy should be treated for 6-12 months with dapsone plus rifampin. This regimen should be followed by treatment with dapsone as monotherapy for 3 years in patients with tuberculoid leprosy or 5 years in patients with borderline lepromatous leprosy. Multibacillary leprosy should be treated for months with dapsone 100 mg/day, clofazimine 50 mg/day and rifampin 600 mg plus clofazimine 300 mg/month. Increasing resistance in patients treated for leprosy has been reported in Southeast Asia. The drug most commonly found to be resistant is dapsone, often in the context of prior exposure or treatment attempts with monotherapy.

More effective and safer compounds should allow simpler and shorter multiple-drug regimes, with a reduced risk of interactions with HIV/AIDS drug treatment or with immunosuppressive and cytotoxic drugs. The development of drug-resistant strains is a continuous biological process, accelerated by the noncompliance with the available regimes and the increase of moderately severe and severe forms of imunodepression in low- and high-income countries. The treatment and prevention of diseases caused by microorganisms of the *Mycobacterium* genus (e.g., *Mycobacterium tuberculosis*, nontuberculous mycobacteria and *Mycobacterium leprae*) requires, urgently, an investment in the research and development of new compounds.

Therefore, the technical problem solved in the present invention is to provide further pharmaceutical active compounds for the prevention and treatment of tuberculosis, as well as diseases caused by nontuberculous mycobacteria or caused by *Mycobacterium leprae*.

Surprisingly, the inventors have found that the compounds of formula I are effective in the prevention and treatment of tuberculosis, diseases caused by nontuberculous mycobacteria and/or caused by *Mycobacterium leprae*.

SUMMARY OF THE INVENTION

The invention provides quinolyl-hydrazones of Formula I, or pharmaceutically acceptable salts, esters, solvates, isomers and prodrugs thereof as well as pharmaceutical compositions containing these compounds for use in the prophylactic and/or therapeutic treatment of tuberculosis and related diseases, such as, diseases caused by nontuberculous mycobacteria and/or caused by *Micobacterium leprae*.

Compounds of the present invention are represented by the following Formula I:

where Q is

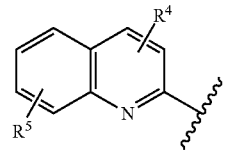

and

A is a 5-6 member substituted or unsubstituted aryl or heteroaryl ring selected from:

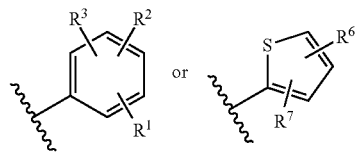

wherein $R^1$, $R^2$ and $R^3$ are each independently of one another, hydrogen, $(C_1-C_4)$alkyl, hydroxyl, halogen, methoxy or methoxy-acetic acid;

and $R^4$, $R^5$, $R^6$ and $R^7$ are each independently of one another, hydrogen or $(C_1-C_4)$ alkyl, and pharmaceutical acceptable salts, esters, solvates, isomers and prodrugs thereof.

Preferred compounds of the general Formula I are represented by the following Formula Ia:

Formula (Ia) compounds are represented by:

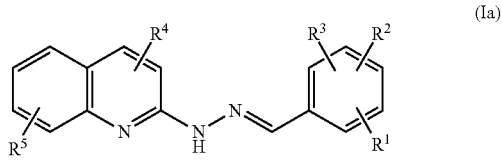

wherein $R^1$, $R^2$ and $R^3$ are each independently of one another, hydrogen, $(C_1-C_4)$alkyl, hydroxyl, halogen, methoxy or methoxy-acetic acid;

and $R^4$ and $R^5$ are each independently of one another, hydrogen or $(C_1-C_4)$ alkyl, and pharmaceutical acceptable salts, esters, solvates, isomers and prodrugs thereof.

Most preferred compounds of the present invention are selected from the group consisting of: —5-bromo-2-hydroxybenzaldehyde 2-quinolinylhydrazone, and 2-hydroxybenzaldehyde-(4-methyl-2-quinolinyl)hydrazone.

Further embodiments of the present invention contemplate pharmaceutically acceptable salts, esters, solvates, isomers and prodrugs of compounds of Formula I and pharmaceutical compositions comprising a compound of Formula I, or a pharmaceutically acceptable salt, ester, solvate, isomer or prodrug thereof, in combination with a pharmaceutically acceptable diluent or carrier for use in the treatment and/or prevention of tuberculosis and related diseases, such as diseases caused by nontuberculous mycobacteria and/or caused by *Micobacterium leprae*.

DETAILED DESCRIPTION OF THE INVENTION

Figure 1:
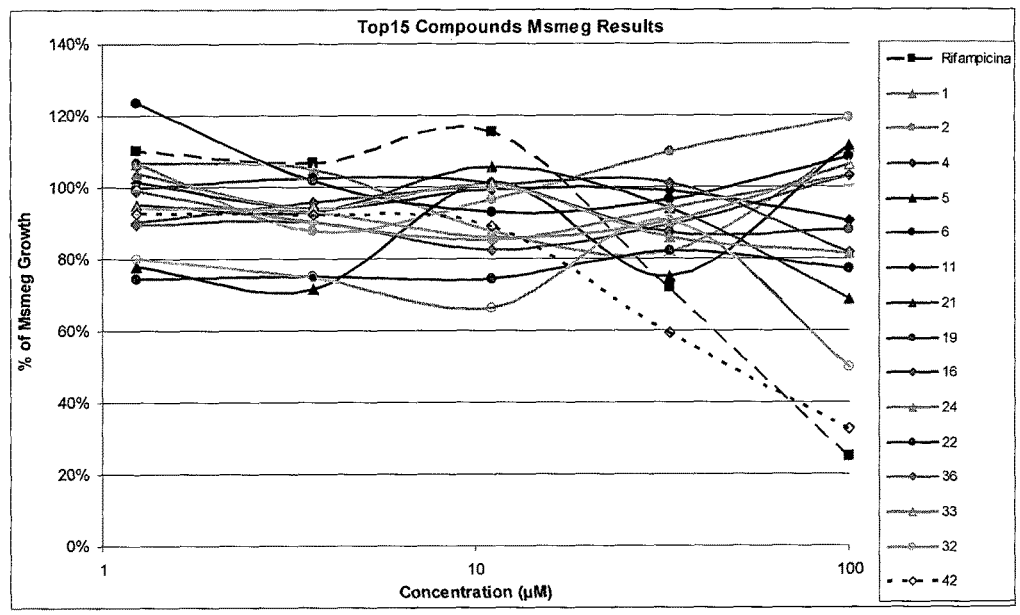
FIG. 1 illustrates *Mycobacterium smegmatis* growth inhibition results for tested compounds.

In one aspect of the present invention, there is provided a compound represented by the following Formula I:

$$Q\underset{H}{\overset{}{N}}\diagdown N\diagup A \quad (I)$$

where Q is

[quinoline structure with $R^4$ and $R^5$ substituents]

and A is a 5-6 member substituted or unsubstituted aryl or heteroaryl ring selected from:

[phenyl with $R^1$, $R^2$, $R^3$ substituents] or [thiophene with $R^6$, $R^7$ substituents]

wherein
$R^1$, $R^2$ and $R^3$ are each independently of one another, hydrogen, $(C_1-C_4)$alkyl, hydroxyl, halogen, methoxy or methoxy-acetic acid;
and
$R^4$, $R^5$, $R^6$ and $R^7$ are each independently of one another, hydrogen or $(C_1-C_4)$ alkyl,
and pharmaceutical acceptable salts, esters, solvates, isomers and prodrugs thereof.

In the context of the present invention the term "$(C_1-C_4)$ alkyl" means methyl, ethyl, n-propyl, iso-propyl, n-butyl, sec-butyl or tert-butyl, and the term "halogen" means fluorine, chlorine, bromine or iodine.

In a further aspect of the present invention, there is provided compounds falling under the definition of the general Formula I and represented by the following Formula Ia:

Formula (Ia) compounds are represented by:

[Structure of Formula (Ia): quinoline with $R^4$, $R^5$ connected via NH-N=CH to phenyl with $R^1$, $R^2$, $R^3$]

wherein $R^1$, $R^2$, $R^3$, $R^4$ and $R^5$ have the same meaning as defined above.

In yet another aspect of the present invention, there are provided compounds of Formula I selected from the group consisting of 5-bromo-2-hydroxybenzaldehyde 2-quinolinylhydrazone and 2-hydroxybenzaldehyde-(4-methyl-2-quinolinyl)hydrazone.

In a further aspect of the present invention, there is provided a compound of Formula I and/or Ia, or a pharmaceutical acceptable salt, ester, solvate, isomer or prodrug thereof, useful for the treatment of a disease in a mammal, such as a human.

In yet another aspect of the present invention there is provided a pharmaceutical composition comprising: (a) a therapeutically effective amount of a compound of Formula I and/or Ia, or a pharmaceutical acceptable salt, ester, solvate, isomer or prodrug thereof; and (b) a pharmaceutically acceptable excipient useful for the treatment of a disease in a mammal, such as human.

In a further aspect of the present invention, there is provided a compound of Formula I and/or Ia, or a pharmaceutical acceptable salt, ester, solvate, isomer or prodrug thereof, or a pharmaceutical composition comprising said compound for inhibiting pantothenate synthetase enzyme activity.

In a yet a further aspect of the present invention, there is provided a compound of Formula I and/or Ia, or a pharmaceutical acceptable salt, ester, solvate, isomer or prodrug thereof, or a pharmaceutical composition comprising said compound for preventing and/or treating tuberculosis and related diseases, such as diseases caused by nontuberculous mycobacteria and/or caused by *Micobacterium leprae*.

The present invention is intended to encompass all pharmaceutically acceptable ionized forms (e.g., salts) and solvates (e.g., hydrates) of the compounds of Formula I and Ia, regardless of whether such forms and solvates are specified, as it is well known in the art that pharmaceutical agents in an ionized or solvated form may be used.

Compounds of Formula I and Ia may contain one or more chiral centers and exist in optically active forms. When a compound of Formula I and/or Ia or a salt thereof contains a single chiral center, it may exist in two enantiomeric forms. The present invention includes individual enantiomers and mixtures of these enantiomers, which may be obtained by methods known to those skilled in the art.

When a compound of Formula I and Ia or a salt thereof contains more than one chiral center it may exist in diastereomeric forms. The present invention includes each diastereomer and mixtures of these diastereomers, which may be obtained by methods known to those skilled in the art.

The compounds under Formula I and Ia may form organic and inorganic salts, for example, with inorganic or organic acids, e.g., hydrochloric acid, hydrobromic acid, fumaric acid, tartaric acid, citric acid, sulfuric acid, maleic acid, acetic acid, succinic acid, benzoic acid, palmitic acid, dodecanoic acid and acidic aminoacids, such as glutamic acid, alkali metal hydroxides, e.g., sodium hydroxide, with amino acids, e.g., lysine or arginine. The salts formed with compounds under Formula I and Ia, provided that they are pharmaceutically acceptable may be used in the present invention. Such salts and corresponding solvates also fall within the scope of the present invention.

Prodrugs of the compounds under Formula I and Ia are also the subject of the present invention. As is known in the art, prodrugs are altered in vivo and become a compound of the present invention. All standard methods of using the compounds of the present invention are intended, whether prodrug delivery is specified, to encompass the administration of a prodrug that is converted in vivo to a compound according to the present invention A variety of routes of administration of the compounds and compositions of the present invention are possible including, but not necessarily limited to parenteral (e.g., intravenous, intra-arterial, intramuscular, subcutaneous injection), oral (e.g., dietary or by inhalation), topical, nasal, rectal, or via slow release micro-carriers, depending on the disease or condition to be treated. Oral, parenteral and intravenous administrations are preferred modes of administration. The formulation of the compounds of the present invention to be administered will vary according to the route of administration selected (e.g., solution, emulsion, gel, aerosol, capsule). Further dosage forms according to the present invention are, for example, solutions, suspensions, ointments, creams, pastes, gels, tinctures, lip-sticks, drops, syrups, aerosols and sprays.

An appropriate composition of the present invention comprising the compound or compounds of Formula I and/or Ia can be prepared in a physiologically acceptable vehicle or carrier and optional adjuvant and preservatives. For solutions or emulsions, suitable carriers include, for example, aqueous or alcoholic/aqueous solutions, emulsions or suspensions, including saline and buffered media, sterile water, creams, ointments, lotions, oils, pastes and solid carriers. Parenteral vehicles can include sodium chloride solution, Ringer's dextrose, dextrose and sodium chloride, lactated Ringer's or fixed oils. Intravenous vehicles can include various additives, preservatives, or fluid, nutrient or electrolyte replenishers. (See Remington's Pharmaceutical Science, 16$^{th}$ Edition, Mack, Ed. (1980))

The preferred compositions for parenteral administration are under the form of solutions, suspensions, emulsions, dispersions and lyophilized compositions of the compounds of the invention, preferably in the form of isotonic aqueous solutions, dispersions, emulsions or suspensions. These compositions are preferably sterile, either being processed in a sterile environment during their whole preparation process or by being sterilized in the end of said process. Furthermore, their manufacture is usually carried out under sterile conditions, as is the filling, for example, into ampoules or vials, and the sealing of the containers. These compositions may be ready to apply or be presented under solid form (for example as a lyophilizate) requiring reconstitution prior application.

Parenteral compositions according to the present invention may comprise excipients, for example vehicles, stabilizers (reducing agents, anti-oxidants and/or sequestering agents), buffering agents, preservatives, isotonizing agents, emulsifiers, solubilizers, viscosity increasing agents, and/or bulking agents and are prepared by conventional processes well known to those knowledgeable of the art.

Non-limiting examples of vehicles, in the context of the present invention, include water for injections, oily vehicles, polyethylene glycol, benzyl alcohol, ethanol and glycerol.

Non-limiting examples of oily vehicles in the context of the present invention include fatty acid esters and mixtures of fatty acid esters, vegetable oils, synthetic oils and semi-synthetic oils, almond oil, castor oil, cottonseed oil, groundnut oil, olive oil, sesame oil, and soybean oil.

Non-limiting examples of reducing agents in the context of the present invention include sodium sulfite, sodium bisulfite and sodium metabisulfite.

Non-limiting examples of anti-oxidants in the context of the present invention include butylated hydroxyanisole, gallic acid esters and tocopherols.

Non-limiting examples of sequestering agents in the context of the present invention include ethylenediaminetetraacetic acid in the form of sodium salt (EDTA), tartaric acid, thiourea and monothioglycerol.

Non-limiting examples of buffering agents in the context of the present invention include the combination of monosodium phosphate with disodium itself, trisodium phosphate, urea, sodium borate and sodium citrate.

Non-limiting examples of preservatives in the context of the present invention include methylparaben, the cresols, benzyl alcohol and phenyllic alcohol.

Non-limiting examples of isotonizing agents in the context of the present invention include boric acid, calcium gluconate, chlorobutanol, potassium chloride, sodium citrate, sodium borate, sodium phosphate, sodium chloride and sodium lactate.

Non-limiting examples of emulsifiers in the context of the present invention include lecithins, monoglycerides, polyethylene polymers and polypropylene polymers.

Non-limiting examples of solubilizers in the context of the present invention include ethanol, polypropylene glycol, N,N-dimethylacetamide or polyoxyethylene sorbitan esters.

Non-limiting examples of viscosity-increasing agents in the context of the present invention include sodium carboxymethylcellulose, carboxymethylcellulose, dextran, polyvinylpyrrolidone or gelatins.

Non-limiting examples of bulking agents in the context of the present invention include mannitol, lactose, sucrose, trehalose, sorbitol, glucose, raffinose, arginine, glycine, histidine, dextran or polyethylene glycol.

Pharmaceutical oral compositions in the solid oral form (tablets, soft capsules, hard capsules or any other) according to the present invention comprise excipients, provided they are compatible with the active ingredient of the composition, including, but not limited to, diluents, binders, disintegrants, surfactants, glidants, lubricants, antioxidants or free radicals sequestrants, coating components, opacifiers or plasticizers.

Soft capsules in the context of the present invention consist of gelatin or any other suitable substance containing the compounds of the invention dissolved, emulsified or suspended in a suitable soft capsule vehicle and optionally excipients such as stabilizers (reducing agents, anti-oxidants and/or sequestering agents, as defined above), solubilizers (as defined above), plasticizers or others. Hard capsules in the context of the present invention may in addition to the compounds of the invention also optionally contain excipients such as fillers, glidantes or others.

Non-limiting examples of diluents in the context of the present invention include cellulose preparations, calcium phosphates, anhydrous lactose, monohydrate lactose, dihydrate lactose, sorbitol, starch, pregelatinized starch, sucrose and mannitol.

Non-limiting examples of binders in the context of the present invention include sodium carboxymethyl cellulose, microcrystalline cellulose, hydroxypropylmethylcellulose, methylcellulose, hydroxypropylcellulose, povidone, a starch paste, pregelatinized starch and sucrose.

Non-limiting examples of disintegrants in the context of the present invention include sodium carboxymethyl cellulose, microcrystalline cellulose, croscarmellose sodium, crospovidone, hydroxypropylcellulose, povidone, poloxamer, starch, sodium lauryl sulfate, starch, pregelatinized starch sodium glycolate, alginic acid or a salt thereof, such as sodium alginate.

Non-limiting examples of surfactants in the context of the present invention include poloxamer and sodium lauryl sulfate.

Non-limiting examples of glidants in the context of the present invention include calcium silicate, starch, talc, colloidal silicon dioxide, magnesium stearate and sodium aluminum silicate.

Non-limiting examples of lubricants in the context of the present invention include sodium stearyl fumarate, sodium lauryl sulfate, talc, silicic acid, stearic, acid or salts thereof, such as magnesium or calcium stearate, and/or polyethylene glycol, or derivatives thereof.

Non-limiting examples of antioxidants and free radical scavengers in the context of the present invention include butilhidroxiltoluen, butilhidroxilanisol, citric acid and citrate salts, ascorbate salts and ascorbate, alpha-tocopherol, sodium acetate, sodium sulphite and compound with organic thiol function.

Non-limiting examples of coating components in the context of the present invention include concentrated sugar solutions, gum arabic, talc, polyvinylpyrrolidone, polyethylene glycol, titanium dioxide, coating solutions in suitable organic or mixed solvents, cellulose phtalates (acetylcellulose phthalate or hydroxypropylmethylcellulose phthalate).

Non-limiting examples of plasticizers in the context of the present invention include glycerol and sorbitol.

Non-limiting examples of soft capsule vehicles in the context of the present invention include fatty oils, paraffin oil, liquid polyethylene glycols or ethylene/propylene glycol fatty acid esters.

Suppositories according to the present invention comprise a compound of the present invention admixtured with a suppository base and optionally further excipients.

Non-limiting examples of suppository bases in the context of the present invention include natural or synthetic triglycerides, paraffin hydrocarbons, polyethylene glycols or higher alkanols (alkanols with at least eight carbon atoms).

The term "pharmaceutically acceptable carrier" as used in the present invention includes any solvent, dispersion media, coatings, antibacterial, and antifungal agents, isotonic and absorption delaying agents, and the like which are compatible with the activity of the compounds and are physiologically acceptable to the subject.

"Effective amount" a used in the present invention includes the amount of the compound or a pharmaceutically acceptable salt thereof, ester, isomer, solvate, or prodrug thereof which allows it to perform its intended function, i.e., prevention of onset or treatment of tuberculosis or related diseases such as caused by nontuberculous mycobacteria and/or caused by Mycobacterium leprae.

A therapeutically effective amount of the active substance of the present invention can be administered by an appropriate route in a single dose or multiple doses.

The therapeutically effective amount will depend upon a number of factors, including biological activity, mode of administration, frequency of treatment, type of concurrent treatment, if any, age, body weight, sex, general health, severity of the condition to be treated, as well as appropriate pharmacokinetic properties. One skilled in the art can determine the appropriate dosage based on the above factors.

The compounds of the invention may be administered initially in a suitable dosage that may be adjusted as required, depending on the clinical response. In general, satisfactory results may be obtained when the compounds of the invention are administered to a human at a daily dosage of between 0.01 mg and 5000 mg (measured as the solid form). A preferred dose ranges between 0.01 and 750 mg/Kg, more preferably between 0.05 and 150 mg/Kg.

The compound can be administered in the form of pharmaceutical compositions comprising the compound once a day or at different times within the day, prophylactically or therapeutically, preferably in an amount effective against tuberculosis or the related disease, to a mammal, for example a human, requiring such treatment. In the case of an individual having a bodyweight of about 70 kg, the daily dose of the mixture administered is from approximately 0.01 g to approximately 50 g, preferably from approximately 0.05 g to approximately 10 g, of a compound of Formula I and/or Ia.

The pharmaceutical compositions of the present invention comprise from approximately 5% to approximately 95% of a mixture of a compound of formula I.

The pharmaceutical compositions of the present invention may, if desired, be formulated so as to provide an immediate or modified release of the active ingredient after administration to the patient.

Unit dose administration forms according to the present invention comprise from approximately 20% to approximately 90% of the compound of formula I, and forms that are non-unit dose type from approximately 5% to approximately 20% of the mentioned compound.

Unit dose forms according to the present invention refer to, for example, coated and uncoated tablets, microcapsules, soft and hard capsules, pellets, powdered doses, ampoules, vials and suppositories.

The present invention relates especially to the use of a compound of formula I and/or Ia or a pharmaceutical acceptable salt, ester, isomer, solvate and/or prodrug, as such or in the form of a pharmaceutical formulation with at least one pharmaceutically acceptable carrier for the therapeutic and also prophylactic treatment of tuberculosis.

The pharmaceutical compositions of the invention are not only useful for the prevention and treatment of tuberculosis, i.e. a disease caused by *Mycobacterium tuberculosis* complex (MTbC), but also for the treatment of diseases caused by related bacteria, in particular *Mycobacterium leprae*, and caused by nontuberculous mycobacteria (NTM).

Mycobacterial diseases are caused by organisms of the *Mycobacterium tuberculosis* complex (MtbC) like *Mycobacterium tuberculosis* (Mtb), *Mycobacterium bovis*, *Mycobacterium africanum*, *Mycobacterium canetii* and *Mycobacterium microti*. Mycobacteria other than MtbC and *Mycobacterium leprae* are known as non-tuberculous mycobacteria (NTM) and can cause also human and animal diseases as is the case for *Mycobacterium avium* complex (MAC), *Mycobacterium smegmatis*, *Mycobacterium gordonae*, *Mycobacterium kansasii*, *Mycobacterium terrae*,

*Mycobacterium scrofulaceum, Mycobacterium vaccae, Mycobacterium marinum, Mycobacterium lentiflavum, Mycobacterium fortuitum, Mycobacterium chelonae, Mycobacterium abscessus, Mycobacterium intracellulare* and *Mycobacterium avium*.

As above mentioned, multidrug-resistant TB (MDR-TB) is defined by resistance to the two most commonly used drugs in the current four-drug (or first-line) regimen, INH and RMP. Drug-resistant TB is the man-made result of interrupted, erratic, or inadequate TB therapy, and its spread is undermining efforts to control the global TB epidemic. Multidrug resistant (MDR-TB) and extensively drug resistant tuberculosis (XDR-TB) develop when the long, complex, decades-old TB drug regimen is improperly administered, or when people with TB stop taking their medicines before the disease has been fully eradicated from their body. Extensively drug resistant tuberculosis (XDR-TB) is defined as TB that is resistant to any fluoroquinolone, and at least one of three injectable second-line drugs (capreomycin, kanamycin, and amikacin), in addition to INH and RMP.

The pharmaceutical compositions of the invention are effective in the treatment and prevention of all forms of tuberculosis such as primary tuberculosis disease, post-primary pleuro-pulmonary tuberculosis disease, post-primary extra-pulmonary tuberculosis disease involving at least one organ or system such as, but not restricted to, lymph nodes, kidney, central nervous system, osteoarticular systems, gastrointestinal system tract, eye, skin and soft tissues or urogenital system, disseminated tuberculosis and reactivated tuberculosis.

The pharmaceutical compositions of the invention are effective in the treatment and prevention of all forms of tuberculosis in adults, children and elderly patients, with or without immunodepression conditions such as, but not restricted to, diabetes mellitus, chronic renal insufficiency, malnutrition, alcoholism, human immunodeficiency virus infection (HIV)/acquired immunodeficiency syndrome. (AIDS), silicosis, paracoccidioidomycosis, leukemias, solid tumors, immunosuppressive drug treatments and hereditary diseases or syndromes.

The pharmaceutical compositions of the invention are effective in the treatment and prevention of diseases caused by nontuberculous mycobacteria that included at least one organ or system such as, but not restricted to, lungs and endobronchial tree, lymph nodes, kidney, central nervous system, osteoarticular system, gastrointestinal system, eye, skin and soft tissues, urogenital system, disseminated and reactivated forms of disease.

The pharmaceutical compositions of the invention are effective in the treatment and prevention of diseases caused by nontuberculous mycobacteria in adults, children and elderly patients, with or without immunosuppressive conditions such as, but not restricted to, diabetes mellitus, chronic renal insufficiency, malnutrition, alcoholism, human immunodeficiency virus infection (HIV)/acquired immunodeficiency syndrome (AIDS), leukemias, solid tumors, immunosuppressive drug treatments and hereditary diseases or syndromes.

The pharmaceutical compositions of the invention are effective in the treatment and prevention of diseases caused by *Mycobacterium leprae* that included at least one organ or system such as, but not restricted to, skin and soft tissues, urogenital system and central nervous system, disseminated and reactivated forms of disease.

The pharmaceutical compositions of the invention are effective in the treatment and prevention of diseases caused by *Mycobacterium leprae* in adults, children and elderly patients, with or without immunosuppressive conditions such as, but not restricted to, diabetes mellitus, chronic renal insufficiency, malnutrion, alcoholism, human immunodeficiency virus infection (HIV)/acquired immunodeficiency syndrome (AIDS), leukemias, solid tumors, immunosuppressive drug treatments and hereditary diseases or syndromes.

Obtaining the Compounds of the Present Invention

All compounds are available at Chembridge Corporation (www.chembridge.com), however the skilled technician can easily obtain them by applying various synthetic methods described in the literature:

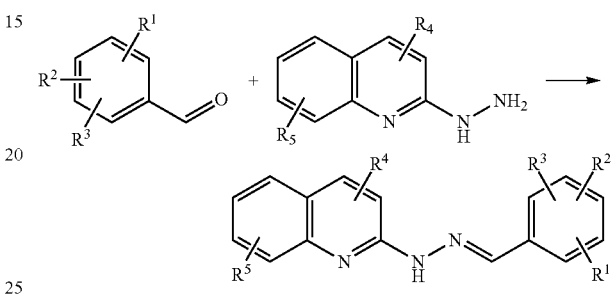

Method for Obtaining Compounds of Formula I, in Particular, Compounds of Formula Ia Reaction of 2-chloroquinoline with hydrazine hydrate at a reflux temperature results in the formation of 2-hydrazinoquinoline.

Further condensation with different aldehydes (for instance, in ethanol at a reflux temperature) gives the corresponding hydrazone. Marckwald; Meyer; *Chemische Berichte*; vol. 33; (1900); p. 1885

Obtaining the Pharmaceutical Compositions of the Present Invention

The pharmaceutical compositions of the present invention are prepared in a manner known per se, for example by means of conventional mixing, granulating, coating, dissolving, emulsifying or lyophilizing processes. Optionally, the manufacture of the compositions according to the present invention includes more steps such as liposomal encapsulation.

In particular, a tablet may be made by compression and molding, optionally with one or or more accessory ingredients. Compressed tablets may be prepared by compressing in a suitable machine the active compound of the present invention in a free-flowing form, e.g., a powder or granules, optionally mixed with ingredients, such as, binders, lubricants, inert diluents, surface active or dispersing agents. Molded tablets may de made by molding in a suitable machine, a mixture of the powdered active compound with any suitable carrier.

In particular, a syrup or suspension may be made by adding the active compound of the present invention to a concentrated, aqueous solution of a sugar, e.g., sucrose, to which also any accessory ingredient may be added. Such accessory ingredients may include, flavoring, an agent to retard crystallization of the sugar or an agent to increase the solubility of any other ingredient, e.g., as a polyhydric alcohol, for example, glycerol or sorbitol.

Formulations for rectal administration may be made with a conventional carrier, e.g., cocoa butter or Witepsol S55 (commercial registered trademark). Specific details related to particular aspects of conventional processes of galenic development can be found in Swarbrick and Boylan's "Encyclopedia of pharmaceutical technology" (1988-2001 NY, Published by M. Dekker).

Alternatively, the compounds of the present invention may be made in liposomes or microspheres (or microparticles), such methods essentially comprising dissolving the compounds of the present invention in an aqueous solution, the appropriate phospholipids and lipids added, along with surfactants if required, and the material dialyzed or sonicated, as necessary. Liposomal encapsulation techniques detailed in Claudio Nastruzzi's book "Liposheres in drug targets and delivery: approaches, methods, and applications" (Boca Raton 2005, published by CRC Press) and in Lasic and Papahadjopoulos' "Liposheres in drug targets and delivery: approaches, methods, and applications" (1998 Amsterdam, N.Y., Published by Elsevier).

Development and Validation of a High-Throughput Screening (HTS) Platform

Regarding the experimental phase, a high-throughput screening (HTS) plataform was developed and validated. This HTS plataform involves the targeting of pantothenate synthetase, an enzyme essential to the metabolic pathways of *Mycobacterium tuberculosis*, by using small molecules as potential inhibitors of this enzyme.

The HTS platform was developed, validated and used to screen 50.000 compounds that were obtained from a diverse chemical library supplied by a vendor called Chembridge.

The HTS platform consists in a yeast strain genetically modified to express the *Mycobacterium tuberculosis's* pantothenate synthetase gene (PanC) instead of the regular Pan6 of the wild-type yeast.

Additionally, this PanC yeast strain is completely dependent on the activity of the expressed pantothenate synthetase to survive.

The validation of the platform demonstrated that (in normal conditions):

Wild-type yeast (Control)—shows normal growth;

Yeast without Pan6—shows reduced growth;

Yeast without Pan6 and complemented with PanC—shows normal growth (similar to control);

Yeast without Pan6 and complemented with Pan6—shows normal growth (similar to control which proves that the genetic intervention does not compromise the metabolic processes of the yeast);

Therefore, a potential inhibitor of the pantothenate synthetase enzyme would result in a reduced growth of the PanC yeast strain.

At the end of this phase the obtained results allowed the classification of a ranking of compounds that included the most potent in inhibiting the growth of the yeast that carried the target, pantothenate synthetase of *Mycobacterium tuberculosis*.

Based on the data obtained in the screening assay, a ranking of compounds was established and the top compounds were selected based on a curve fitting approach that allowed the determination of inhibitory concentrations ($IC_{50}$ and $IC_{90}$) for each screened compound.

For each compound, a concentration-response curve was created using a four parameter logistic fit (available in the curve-fitting software IBDS XLfit™ curve fitting software) that allowed the calculation of $IC_{50}$ and $IC_{90}$ values for each compound.

Additionally, an in vitro assay using *Mycobacterium smegmatis* (as a surrogate for anti-*Mycobacterium tuberculosis* activity) was developed, implemented and used to screen the compounds of interest in an experimental assay. It is important to mention that *Mycobacterium smegmatis* is considered to be a valuable tool for screening of compounds potentially active against *Mycobacterium tuberculosis*, not only because of its non-pathogenic profile but also because of the known gene homology between the two mycobacteria species (Andries K et al., A diarylquinoline drug active on the ATP synthase of *Mycobacterium tuberculosis*. Science. 2005; 307:223-227; Chatuverdi V et al., Evaluation of *Mycobacterium smegmatis* as a possible surrogate screen for selecting molecules active against multi-drug resistant *Mycobacterium tuberculosis*. J Gen Appl Microbiol. 2007; 53:333-337; Cho Y, Ioerger T R and Sacchettini. Discovery of Novel Nitrobenzothiazole Inhibitors for *Mycobacterium tuberculosis* ATP phosphoribosyl Transferase (HisG) through virtual screening. J Med Chem. 2008; 51:5984-5992).

The experimental assay with *Mycobacterium smegmatis* involves the incubation of the test items and the control items *Mycobacterium smegmatis* in 5 concentrations (1.24, 3.7, 11, 33 and 100 μM) for 96 hours. In terms of control items, a blank control that will exhibit maximum growth and a positive control that will exhibit inhibited control are used in this assay. The microorganism growth is evaluated by the measurement of the suspension turbidity: the comparison between negative control and compound or positive control turbidity allowed for the evaluation of the growth inhibition due to the compound presence. The positive control compound used was rifampicin (RMP) that was determined to be the most effective against this strain of *Mycobacterium smegmatis*. Additionally, it is important to notice that RMP is a first-line treatment drug used against *Mycobacterium tuberculosis* in the clinical setting.

After obtaining the concentration-response data for each of the compounds tested in this *Mycobacterium smegmatis* screening assay, a curve fitting approach, based on a four parameter curve fit, allowed for the determination of inhibitory concentrations values such as the IC50 that represents the required concentration to inhibit 50% of the *Mycobacterium smegmatis* growth. This assay had the objective of confirming the superior inhibitory activity of the compounds of the present invention over those known from the prior art, such as RMP.

The results obtained through these assays demonstrate that the following compound: 3,5-dibromo-2hydroxybenaldehyde (2-pyridinyl)hydrazine, (compound no. 42) show a superior inhibitory activity against *Mycobacterium smegmati* than the prior art compound RMP.

Further and in order to define analogues of the compound, 3,5-dibromo-2-hydroxybenzaldehyde (2-pyridinyl)hydrazine (compound no. 42) with the desired pharmacological activity, fingerprint and pharmacophore searching methods were carried out using browser-based search engines. In the case of the fingerprint searching method, 2D substructural fragments of 3,5-dibromo-2-hydroxybenzaldehyde (2-pyridinyl)hydrazine (compound no. 42) were used to search online databases for other molecules that share the same 2D substructures and therefore calculate the similarity of both molecules as a function of the number of fragments that they have in common. For the pharmacophore search, the compound 3,5-dibromo-2-hydroxybenzaldehyde (2-pyridinyl)hydrazine (compound no. 42) was used as the pharmacophore model, including the correspondent pharmacophoric pattern that involves its ensemble of steric and electrostatic features, and online databases with pre-computed conformations were searched for analogues. For both methodologies, only the analogues with a similarity higher than 90% were chosen and tested in the same *Mycobacterium smegmatis* assay described above.

The results obtained from this assay locate additional compounds falling under the formula I and Ia bearing the desired pharmacological activity. These compounds are in particular; —5-bromo-2-hydroxybenzaldehyde 2-quinolinylhydrazone, and 2-hydroxybenzaldehyde-(4-methyl-2-quinolinyl)hydrazone.

EXAMPLES

The invention will now be further described by the following working examples, which are preferred embodiments of the invention. These examples are illustrative rather than limiting and it is to be understood that there may be other embodiments that fall within the spirit and scope of the invention as defined by the claims appended hereto.

Example 1

Identification of Compounds with Pantothenate Synthetase Inhibiting Activity

The screening step in the HTS platform consisted in the incubation of the library compounds (50.000 diverse and publically available chemical entities) with the yeast complemented with PanC and the comparison of its growth at the end of 72 hours with the growth observed in the control yeast. This was performed in a high-throughput manner using robotized procedures and 96-wells plaques for the compound and yeast incubation. The screening step involved the use of 5 concentrations of each compound (0.5, 1, 5, 10 and 20 μM). The comparison of the growth observed for the control yeast with the growth observed for each screened compound allowed the determination of growth inhibition percentage for each tested concentration.

At the end of this phase the obtained results allowed the classification of a ranking of compounds that included the most potent in inhibiting the growth of the yeast that carried the target, pantothenate synthetase of *Mycobacterium tuberculosis*.

From this ranking of compounds, the top compounds were selected based on a curve fitting approach that allowed the determination of inhibitory concentrations (IC50 and IC90) for each screened compound.

For each compound, a concentration-response curve was created using a four parameter logistic fit (available in the curve-fitting software IBDS XLfit™ curve fitting software) that allowed the calculation of IC50 and IC90 values for each compound. The fit quality of each curve was determined by the calculation of curve fit quality values ($r^2$).

Example 2

In Vitro Assay with *Mycobacterium smegmatis* for Screening Compounds with Anti *Mycobacterium tuberculosis* Activity Each of the compounds tested and the positive control were incubated with *Mycobacterium smegmatis* in 5 concentrations (100, 33, 11, 3.7 and 1.24 μM) for 96 hours. *Mycobacterium smegmatis* incubation was performed in suspension mode, without agitation, in Middlebrook 7H9 media suplemented with ADC, at 37° C. The microorganism growth was evaluated by the measurement of the suspension turbidity: the comparison between negative control and compound or positive control turbidity allowed for the evaluation of the growth inhibition due to the compound presence. The positive control compound used was RMP that was determined to be the most effective against this strain of *Mycobacterium smegmatis*. Additionally, it is important to notice that RMP is a first-line treatment drug used against *Mycobacterium tuberculosis* in the clinical setting.

Figure 2:
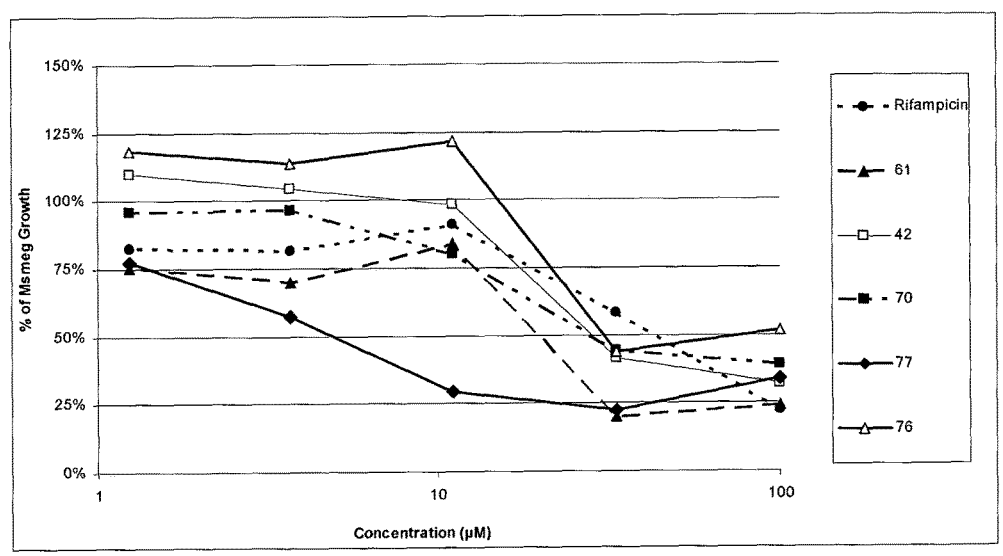
FIG. 2 illustrates *Mycobacterium smegmatis* growth inhibition results for preferred compounds of the invention.

Based on the results, which are shown in FIGS. 1 and 2, we can observe that there was one compound, the compound no. 42, 3,5-dibromo-2-hydroxybenzaldehyde (2-pyridinyl) hydrazine, that exhibited an inhibitory profile of *Mycobacterium smegmatis* growth similar to the one showed by the active control, RMP.

Example 3

Obtaining Analogues of Most Effective Compounds

A series of analogues of the compound, 3,5-dibromo-2-hydroxybenzaldehyde (2-pyridinyl)hydrazine (compound no. 42) were obtained through fingerprint and pharmacophore searching methods and only the analogues with a similarity higher than 90% were chosen and tested in the same *Mycobacterium smegmatis* assay described above. The following table comprise some examples of compounds representative of the whole series:

TABLE 1

Example of Compounds of Formula Ia (Ia)

| Compound no. | $R^1$ | $R^2$ | $R^3$ | $R^4$ | $R^5$ |
|---|---|---|---|---|---|
| 76 | -(2)-OH | H | -(5)-Br | H | H |
| 77 | -(2)-OH | H | H | -(4)-$CH_3$ | H |

The compounds belonging to this Formula Ia showed activity against *Mycobacterium smegmatis*.

Table 2 and FIG. 2 show the growth inhibition results for some specific compounds representatives of the Formula Ia.

TABLE 2

*Mycobacterium Smegmatis* growth inhibition results

| Concentration (uM) | % of Celular Growth at 96 hours | | | |
|---|---|---|---|---|
| | Rifampicin | Compound 42 | Compound 77 | Compound 76 |
| 100.00 | 22.26% | 31.91% | 34.09% | 51.50% |
| 33.33 | 58.04% | 41.52% | 22.41% | 43.92% |
| 11.11 | 90.62% | 98.17% | 29.14% | 121.72% |
| 3.70 | 81.40% | 104.48% | 57.42% | 113.44% |
| 1.23 | 82.55% | 110.06% | 77.17% | 118.35% |

Example 4

Measurement of $IC_{50}$ Value

The inhibitory effect of a compound can be described by an IC50 value, that is the concentration of inhibitor at which half (50%) inhibition of the maximal (100%) inhibition occurs. IC50 values were determined by measuring the extent of inhibition over a range of concentrations of the compounds of interest, preferably a range where the degree of inhibition varied from no inhibition (0%) to complete inhibition (100%). The IC50 value can be estimated from a plot of % inhibition against a concentration of inhibitor, or can be calculated using data fitting programs, such as IDBS XLfit™.

Based on the data obtained in the *Mycobacterium smegmatis* screening assay, a curve fitting approach allowed for the determination of inhibitory concentrations values such as the IC50 that represents the required concentration to inhibit 50% of the *Mycobacterium smegmatis* growth. The lower the $IC_{50}$ the higher the potency of the compounds to inhibit the *Mycobacterium smegmatis*. The IC50 values obtained for specific compounds under Formula Ia were depicted in Table 3.:

TABLE 3

| IC50 Values | |
|---|---|
| Compound | $IC_{50}$ (μM) |
| Rifampicin | 24.82 |
| Compound no. 42 | 15.18 |
| Compound no. 77 | 6.59 |
| Compound no. 76 | 16.18 |

These results showed that the compounds representative of the present invention, namely compounds no. 77 and no. 76 exhibit better $IC_{50}$ values than RMP which translate into more potency for *Mycobacterium smegmatis* inhibition.

As the results demonstrate, surprisingly, the compounds representative of the present invention exhibit better $IC_{50}$ values and more potency than the active control, RMP, thereby confirming its superiority in terms of inhibition of *Mycobacterium smegmatis*.

The invention claimed is:

1. A method of treatment of infections caused by one or more of *Mycobacterium tuberculosis* Complex (MTbC), *Mycobacterium leprae*, and nontuberculous mycobacteria (NTM), comprising administering to a mammal an amount of a pharmaceutical composition comprising at least a compound of general Formula (I):

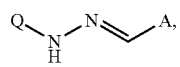

(I)
wherein Q is

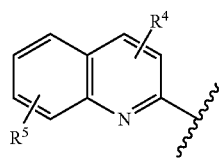

and A is a 5-6 member substituted or unsubstituted aryl or heteroaryl ring selected from:

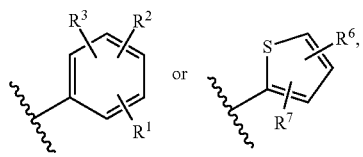

wherein
$R^1$, $R^2$ and $R^3$ are each independently of one another, hydrogen, $(C_1-C_4)$alkyl, hydroxyl, halogen, methoxy or methoxy-acetic acid;
and
$R^4$, $R^5$, $R^6$ and $R^7$ are each independently of one another, hydrogen or $(C_1-C_4)$alkyl,
or a pharmaceutically acceptable salt, ester, solvate, isomer or prodrug thereof.

2. The method of treatment of infections according to claim 1, wherein the infection causes disease selected from the group consisting of primary tuberculosis disease, post-primary pleuropulmonary tuberculosis disease, post-primary extra-pulmonary tuberculosis disease involving at least one organ or system of a mammal.

3. The method of treatment of infections according to claim 1, wherein infections caused by *Mycobacterium tuberculosis* Complex (MTbC) includes infection caused by organisms of the group selected from *Mycobacterium tuberculosis* (Mtb), *Mycobacterium bovis*, *Mycobacterium africanum*, *Mycobacterium canetii* and *Mycobacterium microti*.

4. The method of treatment of infections according to claim 1, wherein infections caused by non-tuberculous mycobacteria (NTM) includes infection caused by organisms of the group selected from *Mycobacterium avium* complex (MAC), *Mycobacterium smegmatis*, *Mycobacterium gordonae*, *Mycobacterium kansasii*, *Mycobacterium terrae*, *Mycobacterium scrofulaceum*, *Mycobacterium vaccae*, *Mycobacterium marinum*, *Mycobacterium lentiflavum*, *Mycobacterium fortuitum*, *Mycobacterium chelonae*, *Mycobacterium abscessus*, *Mycobacterium intracellulare* and *Mycobacterium avium*.

5. The method of treatment of infections according to claim 1, wherein the treatment groups are children or elderly patients.

6. The method of treatment of infections according to claim 1, wherein the treatment group are patients with any immunosuppressive condition.

7. The method of treatment of infections according to claim 1, wherein the treatment comprises administering the pharmaceutical composition to a mammal at a daily dosage of between 0.01 mg/kg body weight and 5000 mg/kg body weight.

8. A method of treatment of infections caused by one or more of *Mycobacterium tuberculosis* Complex (MTbC), *Mycobacterium leprae*, and nontuberculous mycobacteria (NTM), comprising administering to a mammal an amount of the pharmaceutical composition according to claim 1, or a pharmaceutically acceptable salt, ester, solvate, isomer or prodrug thereof that is therapeutically effective for the treatment of infections caused by one or more of *Mycobacterium tuberculosis* Complex (MTbC), *Mycobacterium leprae*, and nontuberculous mycobacteria (NTM).

9. The method of treatment of infections according to claim 1, wherein the compound is represented by Formula (Ia):

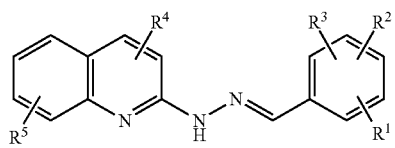

(Ia)

wherein $R^1$, $R^2$ and $R^3$ are each independently of one another, hydrogen, $(C_1-C_4)$alkyl, hydroxyl, halogen, methoxy or methoxyacetic acid; and $R^4$ and $R^5$ are each independently of one another, hydrogen or $(C_1-C_4)$ alkyl, or a pharmaceutically acceptable salt, ester, solvate, isomer or prodrug thereof.

10. The method of infections according to claim 1, wherein the compound is selected from the group consisting of 5-bromo-2-hydroxybenzaldehyde 2-quinolinylhydrazone and 2-hydroxybenzaldehyde-(4-methyl-2-quinolinyl)hydrazone, or a pharmaceutically acceptable salt, ester, solvate, isomer or prodrug thereof.

11. The method of treatment of infections according to claim 1, wherein the compound is a pharmaceutically acceptable salt, ester, solvate, isomer or prodrug thereof.

12. The method of treatment of infections according to claim 1, wherein the pharmaceutical composition comprises a pharmaceutically acceptable salt, ester, solvate, isomer or prodrug thereof and at least a pharmaceutically acceptable excipient.

13. The method of treatment of infections according to claim 1, wherein the composition is in the form of a tablet, coated tablet, microcapsule, soft capsule, hard capsule, pellet, suppository, powder, solution, suspension, aerosol, syrup, drops, cream, paste, gel, ointment, tincture, lipstick and/or spray.

* * * * *